(12) United States Patent  
Eichelberger et al.

(10) Patent No.: US 6,614,969 B2
(45) Date of Patent: Sep. 2, 2003

(54) HIGH SPEED ELECTRONIC REMOTE MEDICAL IMAGING SYSTEM AND METHOD

(75) Inventors: Eric E. Eichelberger, Tualatin, OR (US); Theron V. Page, Jr., West Linn, OR (US)

(73) Assignee: The Ludlow Company, LP, Chicopee, MA (US)

( * ) Notice: Subject to any disclaimer, the term of this patent is extended or adjusted under 35 U.S.C. 154(b) by 93 days.

(21) Appl. No.: 09/966,774

(22) Filed: Sep. 27, 2001

(65) Prior Publication Data

US 2003/0023164 A1 Jan. 30, 2003

Related U.S. Application Data

(63) Continuation-in-part of application No. 09/916,728, filed on Jul. 26, 2001.

(51) Int. Cl.[7] ............................................. G02B 6/44
(52) U.S. Cl. ...................................... 385/101; 385/104
(58) Field of Search .................. 385/100–114, 115–121

(56) References Cited

U.S. PATENT DOCUMENTS 5,329,940 A * 7/1994 Adair ......................... 128/200
5,418,878 A * 5/1995 Sass et al. ................... 385/101
6,338,716 B1 * 1/2002 Hossack et al. ............. 600/459

* cited by examiner

Primary Examiner—Loha Ben
Assistant Examiner—M. Hasan
(74) Attorney, Agent, or Firm—Langlotz Patent Works, Inc.; Bennet K. Langlotz

(57) ABSTRACT

A medical imaging system with a base unit including an electronic display, and a remote imaging transducer connected to the display unit via a flexible cable. The cable includes a number of signal transmission lines, each of which includes a twisted pair of conductors for digital differential signal lines. Each conductor is connected at a first end to the transducer, and at a second end to the base unit. The signal transmission lines may be wrapped about a core, which may be an optical conduit communicating with a light source at the base unit.

12 Claims, 5 Drawing Sheets

HIGH SPEED ELECTRONIC REMOTE MEDICAL IMAGING SYSTEM AND METHOD

REFERENCE TO RELATED APPLICATION

This is a continuation-in-part of U.S. patent application Ser. No. 09/916,728, filed Jul. 26, 2001, entitled CABLE HAVING SIGNAL CONDUCTORS SURROUNDING OPTICALLY TRANSMISSIVE CORE FOR REMOTE IMAGING SYSTEM, which is incorporated by reference herein.

FIELD OF THE INVENTION

This invention relates to medical imaging systems having high speed multiple-wire cables.

BACKGROUND OF THE INVENTION

Remote imaging systems are used to view objects not normally accessible to human observation or conventional optical imaging tools. Only limited-size image transducers are positioned for viewing, and a signal is transmitted to a remote location for viewing. For instance, surgeons use optical imaging probes to view internal anatomy for diagnosis or surgery. Such systems require miniaturized multi-wire cable assemblies to transmit image signals recorded by a charge coupled device (CCD) to an external display screen. Other medical imaging systems use an ultrasound transducer that contacts the patient externally, to transmit an internal image via a multi-wire cable to an instrument for display.

For surgical and other applications, it is desirable to minimize the cable size. Limited diameter facilitates desired flexibility. However, a detailed real-time image needs significant bandwidth, requiring many separate conductors of a given frequency capability. To avoid undesirably bulky cables when substantial numbers of conductors are required, very fine conductors are used. To limit electrical noise and interference at high signal frequencies, conductors are generally shielded. A typical approach employs fine coaxial wires, which are bundled in a cable. Each wire includes its own shield, which provides suitable protection against interference at high frequencies.

While adequate, multiple coaxial assemblies have several disadvantages. The manufacturing cost of fine coaxial wiring is higher than is acceptable for many applications. The mode of terminating very fine coaxial wire is complex and expensive. And coaxial wires generate unwanted bulk due to the need for a given spacing between core conductor and shield.

SUMMARY OF THE DISCLOSURE

The present invention overcomes the limitations of the prior art by providing a medical imaging system with a base unit including an electronic display, and a remote imaging transducer connected to the display unit via a flexible cable. The cable includes a number of signal transmission lines, each of which includes a twisted pair of conductors used for digital differential signaling. These twisted pairs maintain signal integrity without a shield by utilizing the well known advantages of differential signals, namely the elimination of signal radiation and the reduction of common mode interference. Digital systems utilizing differential signaling include LVDS, SCI, Fiber Channel, and Firewire. Each conductor is connected at a first end to the transducer, and at a second end to the base unit. The signal transmission lines may be wrapped about a core, which may be an optical conduit communicating with a light source at the base unit. The system may employ optical or ultrasound imaging.

DETAILED DESCRIPTION OF A PREFERRED EMBODIMENT

Figure 1:
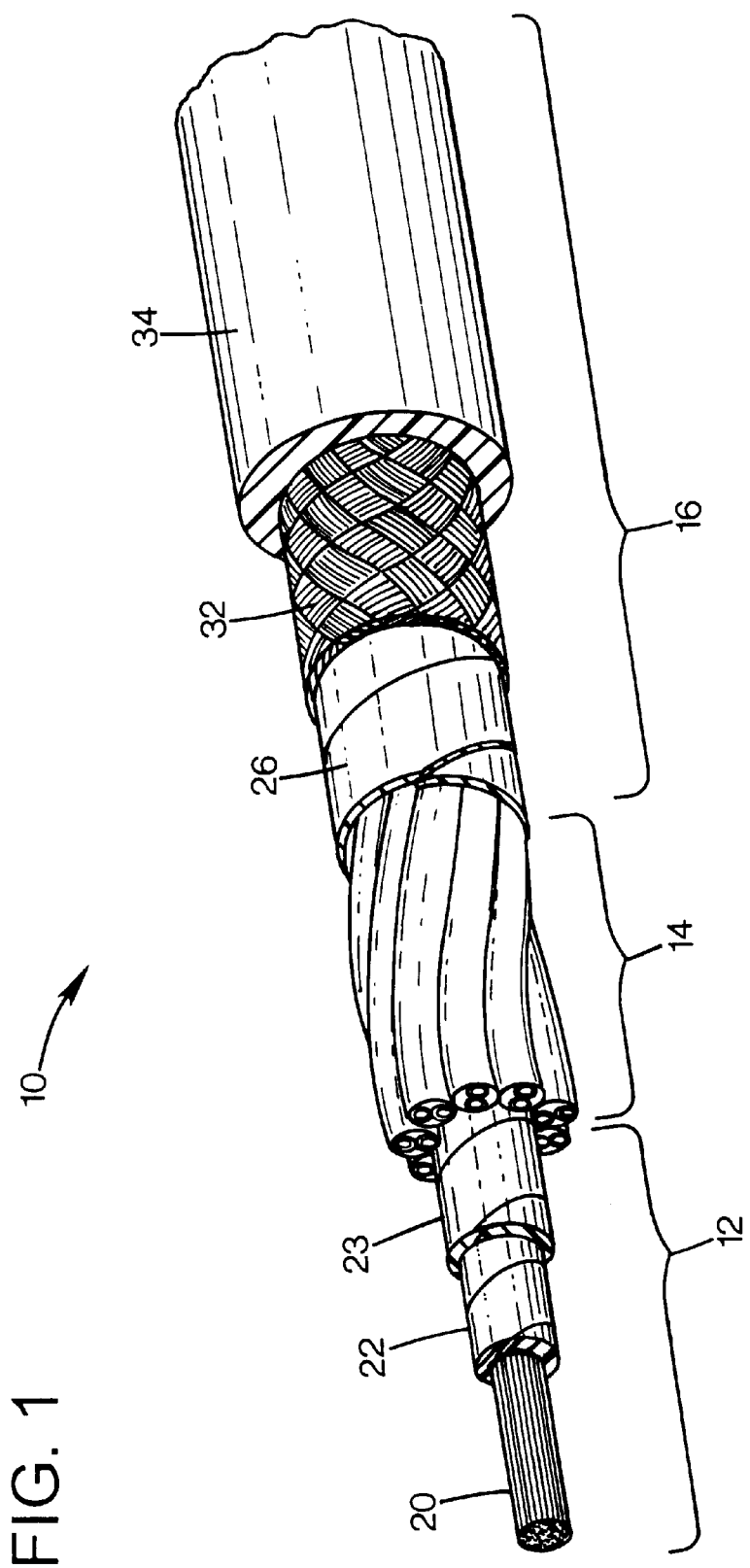
FIG. 1 is a cut-away perspective view of a cable assembly according to a preferred embodiment of the invention.

FIG. 1 shows a flexible cable assembly 10 for high frequency signal or high speed data transmission. The cable includes a core 12, a set of twisted pair wires 14 helically wrapped about the core, and an outer sheath portion 16.

The core has a flexible optical conduit provided by a bundle of light-transmissive optical fibers 20. The fibers are wrapped by a spiral metal armor layer 22 with an inside diameter of 0.160, and an outside diameter of 0.200. The armor layer serves to provide a cylindrical shape that does not deviate in cross section significantly under later pressure, to preserve uniform spacing of the pairs from the axis of the cable. The armor is insulated by a helically-wrapped single band of thin tape 23. The tape is a low-friction fluoropolymer film having a thickness of 0.002 inch, a width of 0.125 inch, and wrapped with 45% overlap. In the preferred embodiment, the conduit is provided by 2050 fibers, each of 0.66 Numerical Aperture and having a 70 micron diameter, with a fiber packing density of 80%, for an overall diameter of 3.5 mm.

The twisted pair wires 14 each include two helically twisted wires insulated from each other and encased in a conformal pair sheath as will be discussed below. Nine twisted pairs are provided, although this number may vary without limitation depending on the needs of the particular application. Each twisted pair sheath has a diameter of 0.030 inch, which allows each to abut the surface of the core throughout its entire length, and to abut each adjacent pair sheath. This ensures that each pair is kept at the same controlled distance from the core conductor, and from the adjacent pairs.

In the preferred embodiment, the pairs wrap helically about the core. The wrap angle results in each pair making one full wrap about the core over a cable length of 2.0 inches. The wrap angle may vary slightly to accommodate variations in pair sheath diameter and core sheath diameter. If the pairs were sized to abut each other and the core, a slight variance of the pair diameter above nominal, or of the core diameter below nominal would cause at least one pair to be forced away from abutment with the core. However, an intended slight under-sizing of the pairs (and/or over-sizing of the core) prevents this problem. In this case, the expected gapping between pairs that would occur if they were parallel to the core is prevented by helically wrapping them. The degree of the wrap angle is in effect determined by the geometry of the pairs and core, with the wrap angle increasing (and the length for one full helical revolution of a pair decreasing) for smaller pair diameters.

The twisted pairs are helically wrapped by a single band of thin tape 26 that holds the pairs against the core during intermediate manufacturing stages, and throughout the life of the cable. The tape is slightly tensioned to bias the pairs against the core, and to prevent gapping when the cable is flexed during usage. The tape is a low-friction fluoropolymer film having a thickness of 0.004 inch. With a tape width of 0.5 inch, and an outside diameter of the pair and core bundle of 0.290 inch, the tape wraps with approximately 3 turns to the inch, with a 30% overlap between wraps.

A conductive shield 32 wraps closely about the bundle. The shield is a braided wrap of 38 AWG copper wire, with a specified coverage of at least 90%. With the controlled dimensions of the spacer sheath, the shield is spaced equally from each wire pair.

An outer sheath 34 closely surrounds the shield with a wall thickness of 0.030 inch, and provides protection against damage. The outer sheath is formed of flexible polyurethane, and is preferably co-extruded about the shield. The finished cable has an exterior diameter of 0.390 inches.

Figure 2:
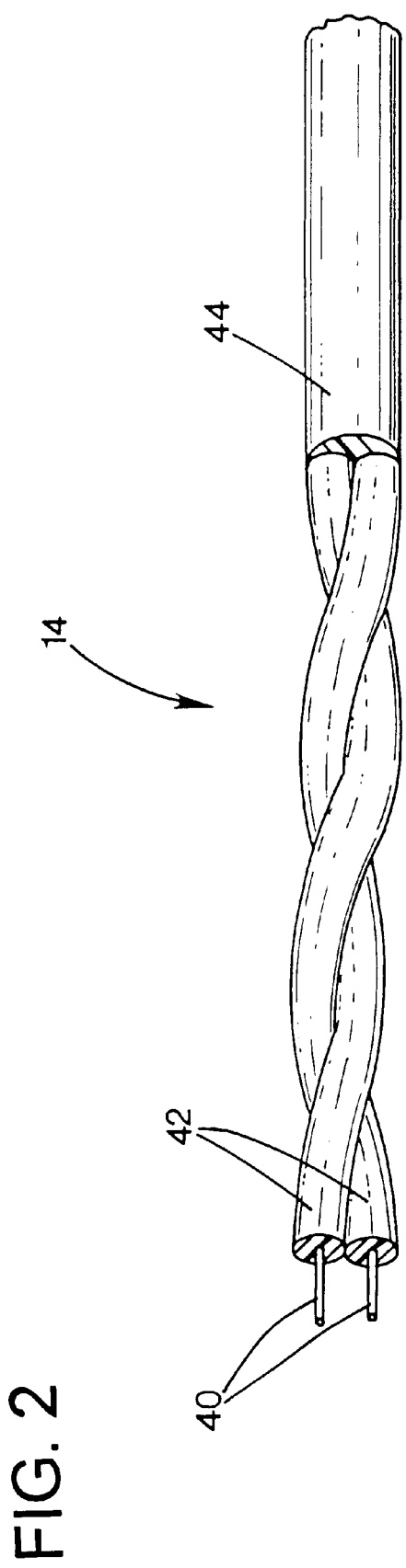
FIG. 2 is a cut-away perspective view of a cable assembly component according to the preferred embodiment of the invention.

FIG. 2 shows a single twisted pair 14 in detail. Each wire of the pair has a conductor 40 of 32 AWG copper, surrounded by an insulating sheath 42 of 0.003 inch wall thickness fluropolymer material. Each sheathed wire has an outside diameter of 0.015 inch. The wires are wound in a helix with a twist rate of 3 full turns per inch. In some applications, the twist rates may be engineered at different rates to avoid unwanted interference between adjacent pairs. For example, the twist rates may alternate between two different values so that adjacent pairs do not interact. The wires are in contact with each other along their entire length, on an axis. In the preferred embodiment, the wires are encased in a cover 44 of polymeric material. The cover is co-extruded about the wires, with an outside diameter of 0.045 inch, or 1½ times the diameter of the pairs.

As illustrated and described in the preferred embodiment, it has been found that the cable enables data rates of 100 to 655 Mbits/sec per pair. This is for cables with a length of 18 to 120 inches. While the very fine wires employed are needed to ensure flexibility for applications where a connected component must be moved comfortably (such as for input devices or transducers connected to computing equipment or electronic instruments), it is believed that longer cable lengths required for other purposes will require larger conductors. Although these may employ the concepts disclosed and illustrated for the preferred embodiment, they are less suited where repeated flexibility is needed.

Figure 3:
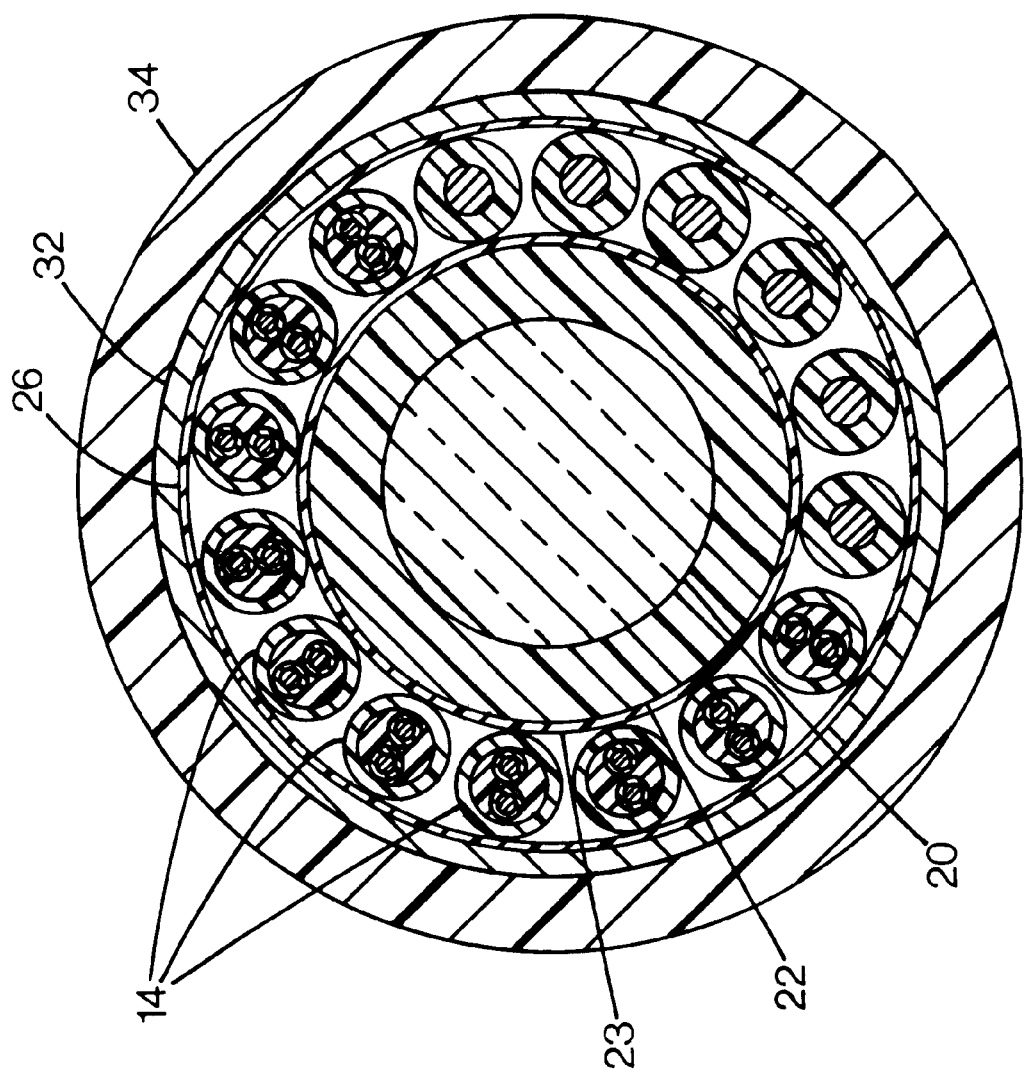
FIG. 3 is a sectional end view of a cable assembly according to the preferred embodiment of the invention.

As shown in FIG. 3, some of the wires wrapped about the core may not be twisted pairs. In the illustrated embodiment, there are six wires having a solid core for power and other higher current needs, while the twisted pairs serve to transmit the low voltage differential signals. In alternative embodiments, all wires may be twisted pairs, or different numbers or proportions of twisted pairs may be used.

Figure 4:
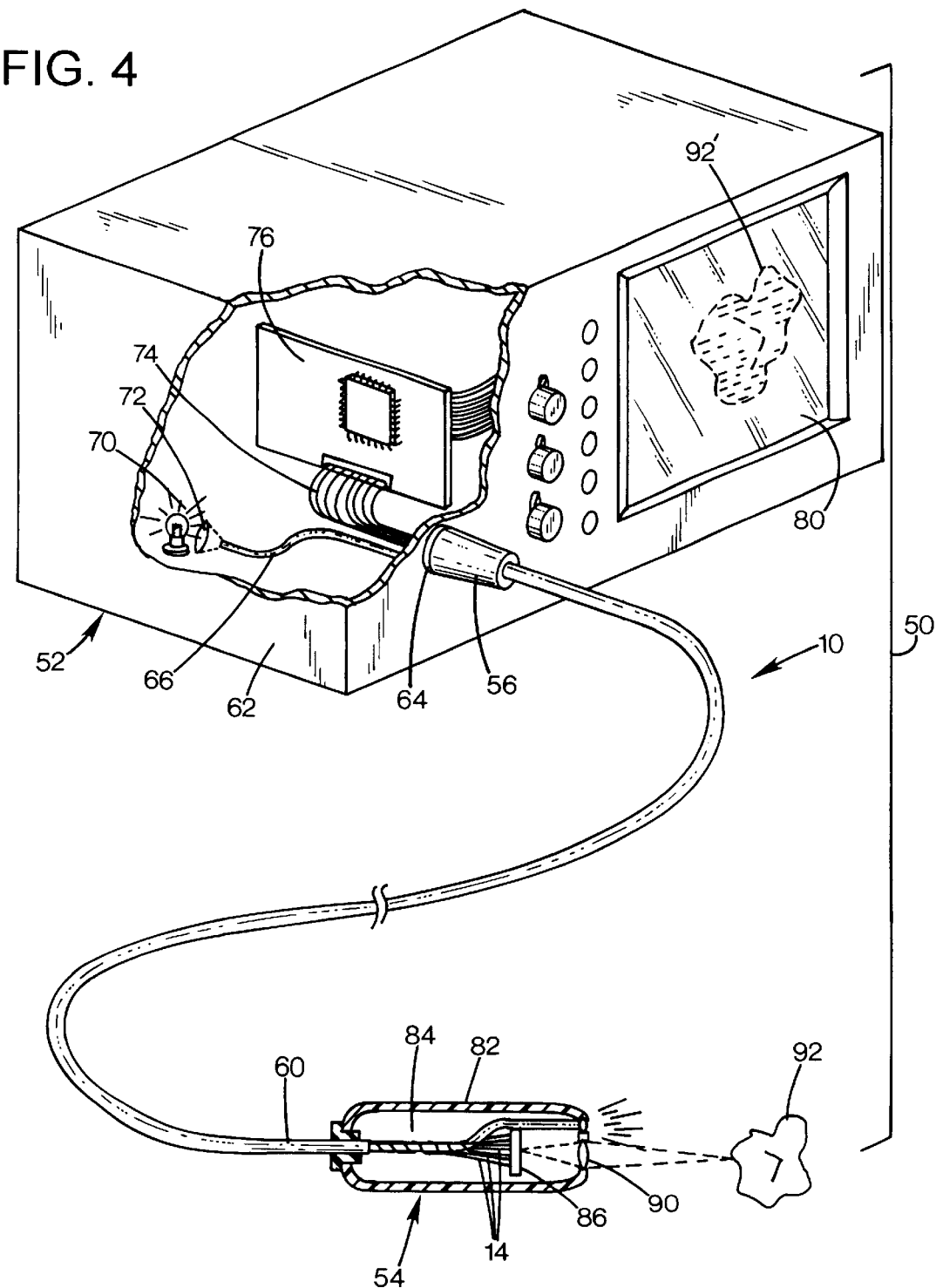
FIG. 4 is a cut-away perspective view of an imaging system employing the cable assembly according to the preferred embodiment of the invention.

The cable 10 is employed in an imaging system 50 as shown in FIG. 4. The system includes an instrument 52, the cable 10, and a camera 54. The cable 10 has a first end 56 connected to the instrument, and a second end 60 connected to the camera.

The instrument has a housing 62 with a connector 64. A fiber optic conduit 66 extends within the housing from the connector 64 to an illumination source such as a light bulb 70, via a concentrating lens 72 that couples the light source to the conduit. A set of electrical wires 74 extends from the connector to an electronic circuit element 76 in the housing. An electronic display screen 80 is electronically connected to the circuitry. The circuitry serves to receive an electronically encoded moving image information via the cable, and decodes it for display on the screen.

The instrument connector includes an interface suitable for coupling the optical conduit 66 in the housing with the optical fiber bundle 20 of the cable. Similarly, the connector includes components to connect the wiring 74 with the wires of the cable. In an alternative embodiment, the cable may be permanently attached to the housing, so that no connector is required, and so that the optical fibers extend fully to the light source, and the cable wires connect directly to the circuitry.

The camera 54 is a compact device having a housing 82 defining a chamber 84 in which a charge-coupled device (CCD) 86 is contained. In alternative embodiments, any electronic image transducer suitable for generating an electronic signal that may be decoded for re-generation of an image formed on the transducer surface may be employed. A lens 90 in the housing is positioned on axis with the imaging surface of the CCD, to form an image of an object 92 on the imaging surface. The wires 14 of the cable are connected to the CCD, so that a corresponding electronic image 92' is displayed on the screen 80.

Illumination of the object is provided by the light transmitted by the fiber optic bundle. The end of the fiber bundle 20 is located adjacent to the imaging lens 90, so that emitted light shines in the direction of the optical axis of the lens. In an alternative embodiment, the fiber ends may be distributed coaxially about the imaging lens. In operation, the camera is positioned away from the instrument, and adjacent to the object imaged. In medical applications, the camera may be internally positioned in a patient. The camera may be mounted together with surgical instruments such as endoscopes.

Figure 5:
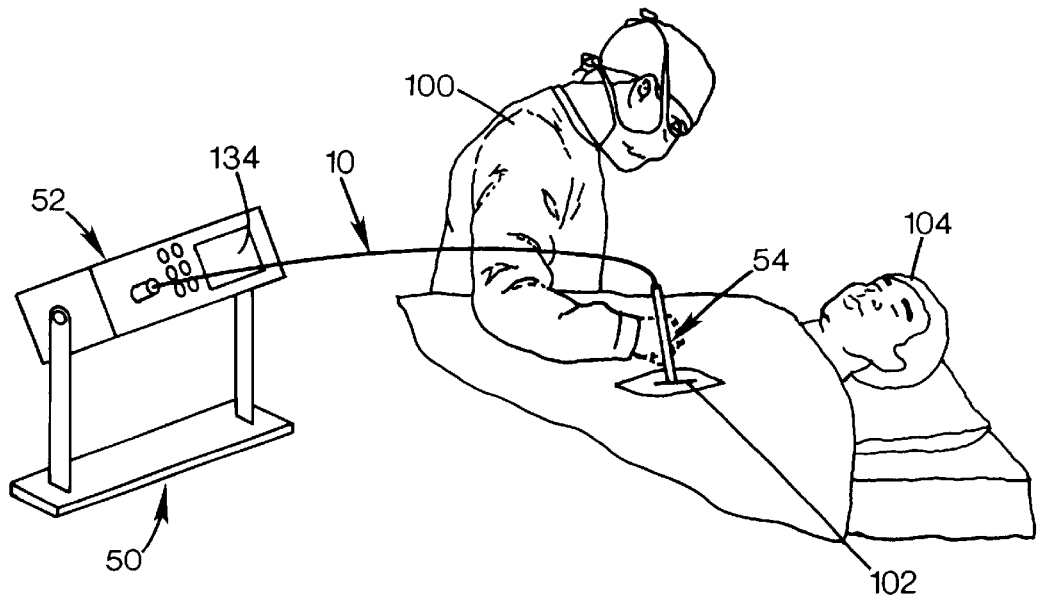
FIG. 5 is a view of an imaging system according to the preferred embodiment of the invention.

For instance, FIG. 5 shows the imaging system 50 in which a surgeon 100 has inserted the camera 54 into an incision 102 in a surgical patient. The light source in the base unit 52 is carried through the optical fibers in the cable 10 to the camera. The light illuminates the field internal to the patient, so that light reflected off the tissues in the patient generates the image on the CCD. This image is converted to an electronic signal that is returned to the base unit via the high speed twisted pairs using Low Voltage Differential Signal (LVDS) transmission, whereupon the signal is converted to an image that is displayed for observation by the surgeon in real time during the surgery. Although illustrated with the display unit integral with the instrument for simplicity, in many applications, a separate display may be positioned within the surgeon's field of view in another location, or the instrument positioned for direct viewing during surgery.

Figure 6:
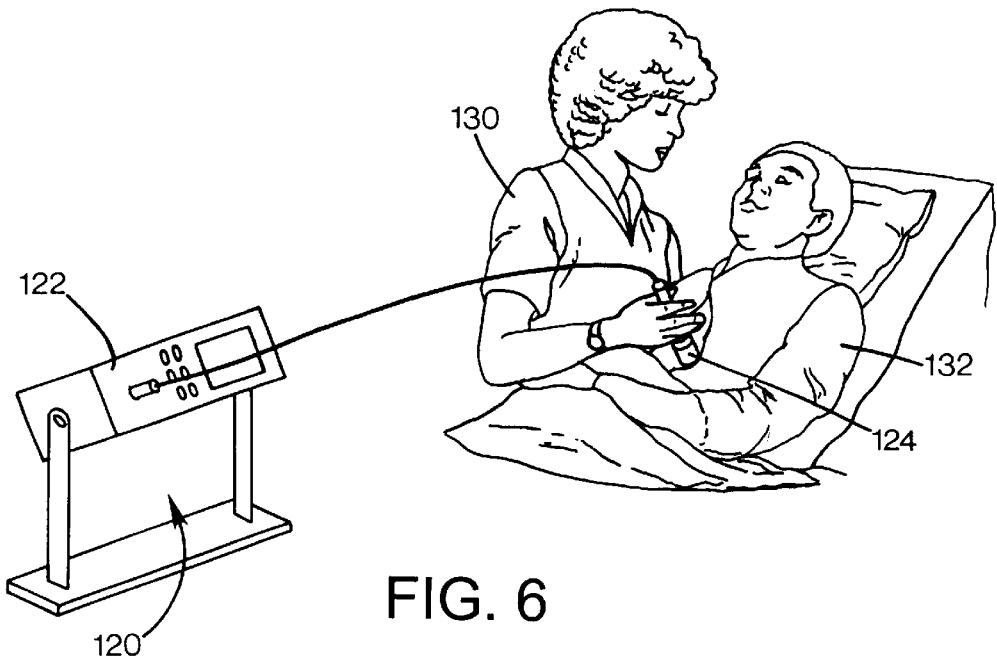
FIG. 6 is a view of an imaging system according to an alternative embodiment of the invention.

FIG. 6 shows an alternative ultrasound medical system 120. An ultrasound base unit 122 has an ultrasound transducer unit 124 connected by a flexible cable 126. The cable 126 is comparable to the cable 10 of FIGS. 1–5, except that it does not employ the optical fiber conduit, since ultrasound imaging does not require illumination. A central core conductor of greater size than the twisted pair conductors may be substituted, and used to provide power to the transducer. The twisted pairs may surround the core in the same manner as in cable 10.

The physician or technician 130 applies the transducer unit externally in contact with the patient 132. Ultrasonic energy is emitted by the transducer into the patient's tissues, which reflect the energy back in a pattern that reveals the nature and position of the tissues. This energy pattern is converted to a high-bandwidth electronic signal that is returned to the base unit via the high speed twisted pairs using Low Voltage Differential Signal (LVDS) transmission. The signal is then reconverted for display as a real time moving image on a display screen 134 on the base unit, for viewing.

While the above is discussed in terms of preferred and alternative embodiments, the invention is not intended to be so limited. For instance, the medical use of twisted pairs for LVDS transmission of signals from flexibly connected transducers need not be limited to endoscopy and ultrasound imaging. Any medical application where images must be made of subjects remote from a display unit may employ such features. This may include external imaging cameras used for dentistry, conventional surgery, robotic surgery, minimally invasive surgery (arthroscopic, laproscopic), internal diagnostics, opthalmic and other fields in which close, high-resolution visual inspection and medical analysis is required and where flexibility of cabling is needed.

What is claimed is:

1. A medical imaging system comprising:
    a base unit including an electronic display;
    a remote imaging transducer connected to the display unit via a flexible cable;
    the cable including a plurality of signal transmission lines; and
    each signal transmission line including a pair of conductors coupled for low voltage differential signal transmission.

2. The system of claim 1 wherein the cable includes an optically transmissive element connected at one end to an illuminator, and operable to transmit light to a subject imaged by the transducer.

3. The system of claim 2 wherein each of the signal transmission lines is wrapped about the optically transmissive element.

4. The system of claim 1 wherein the transducer is a photosensitive electronic device.

5. The system of claim 1 wherein the transducer is an ultrasound element.

6. The system of claim 1 wherein the conductors of each signal transmission line are of a common wire gauge, and are each helically would about each other.

7. The system of claim 1 wherein the signal transmission lines are evenly spaced apart from an axis defined by the core.

8. A method of medical imaging comprising the steps:
    positioning a transducer adjacent a patient;
    generating an electrical signal in the transducer to represent an image;
    transmitting the signal via a flexible cable connected to a base unit, including transmitting separate signals via a plurality of pairs of conductors, employing low voltage differential signal transmission; and
    in the base unit, displaying an image based on the signal.

9. The method of claim 8 wherein transmitting signals includes transmitting signals via twisted pairs of wires.

10. The method of claim 8 including illuminating a subject portion of the patient imaged by the transducer via an optical conduit in the cable.

11. The method of claim 8 wherein generating an electrical signal in the transducer includes forming an image on a photosensitive electronic device.

12. The method of claim 8 wherein generating an electrical signal in the transducer includes receiving emitted ultrasound energy.

* * * * *